United States Patent
Brown et al.

(10) Patent No.: US 6,841,547 B2
(45) Date of Patent: Jan. 11, 2005

(54) METHOD FOR DECREASING LOW DENSITY LIPOPROTEIN

(75) Inventors: David Brown, Bronxville, NY (US); Lorne M. Golub, Smithtown, NY (US); Hsi-Ming Lee, Setauket, NY (US); Robert Greenwald, Melville, NY (US); Maria Ryan, Huntington, NY (US); Kavita Desai, Bronx, NY (US)

(73) Assignees: Albert Einstein College of Medicine of Yeshevia University, Bronx, NY (US); Montefiore Medical Center, Bronx, NY (US); The Research Foundation of State University of New York, Albany, NY (US)

( * ) Notice: Subject to any disclaimer, the term of this patent is extended or adjusted under 35 U.S.C. 154(b) by 14 days.

(21) Appl. No.: 10/377,088

(22) Filed: Feb. 28, 2003

(65) Prior Publication Data

US 2004/0171591 A1 Sep. 2, 2004

(51) Int. Cl.$^7$ .............................................. A61K 31/65
(52) U.S. Cl. ....................................................... 514/152
(58) Field of Search ......................................... 514/152

(56) References Cited

U.S. PATENT DOCUMENTS

2003/0181371 A1 * 9/2003 Hunter et al. .................. 514/12

FOREIGN PATENT DOCUMENTS

WO      WO 02/089843 A1   11/2002

OTHER PUBLICATIONS

Albert, M.A., et al., "Effect of Statin Therapy on C–Reactive Protein Levels", *JAMA* 2001, 286(1):64–74.
Berchev, Kr., et al., "Effect of Chlortetracycline on the Pathogenesis of Experimental Atherosclerosis", *Nauchni Tr, Vissh Med Inst Sofii* 1970, 49(4):43–47.

Bocker, R., et al., "Comparative Evaluation of the Effects of Tetracycline and Doxycycline on Blood and Liver Lipids of Male and Female Mice", *Arzneim–Forsch/Drug Res.* 1981, 31(12):2118–2120.

Korpela, J.T., et al., "Effect of Oxytetracycline on Bacterial Intestinal Metabolism of Neutral Sterols and on Serum Lipids", *Scand J. Gastroenterol* 1984, 19:401–404.

Pigatto, P.D., et al., "Isotretinoin versus Minocycline in Cystic Acne: A Study of Lipid Metabolism", *Dermatologica* 1986, 172:154–159.

Ridker, P.M., et al., "Comparison of C–Reactive Protein and Low–Density Lipoprotein Cholesterol Levels in the Prediction of First Cardiovascular Events", *N. Engl. J. Med.* 2002, 347(20):1557–1565.

Samuel, Paul, et al., "Effect of Neomycin and Other Antibiotics on Serum Cholesterol Levels and on 7α–Dehydroxylation of Bile Acids by the Fecal Bacterial Flora in Man", *Circulation Research* 1973, vol. XXXIII:393–402.

Shaddad, Sania A.I., et al., "The Effect of Oxytetracycline on Growth and Lipid Metabolism in Poultry", *Comp. Biochem. Physiol.* 1985, 80C(2):375–380.

* cited by examiner

*Primary Examiner*—Raymond J. Henley, III
(74) *Attorney, Agent, or Firm*—Hoffmann & Baron, LLP

(57) ABSTRACT

The present invention relates to a method for decreasing elevated serum/plasma LDL-cholesterol levels or LDL-cholesterol levels and CRP levels in a mammal in need thereof. The methods comprises administering an effective amount of a tetracycline formulation. In one embodiment, the tetracycline formulation is a non-antibacterial tetracycline. In another embodiment, the tetracycline formulation is an antibacterial tetracycline at a sub-antibacterial amount.

20 Claims, No Drawings

METHOD FOR DECREASING LOW DENSITY LIPOPROTEIN

BACKGROUND OF THE INVENTION

Cholesterol is vital to a variety of life-sustaining functions, such as serving as a source of fuel, contributing to cell structure, and manufacturing of hormones. For cholesterol to circulate through the blood, cholesterol typically combines with lipoproteins by esterification.

For instance, cholesterol can combine with low density lipoprotein (LDL) to form low density lipoprotein-cholesterol. LDL-cholesterol is a large spherical particle containing a core, which contains about 1,500 molecules of cholesterol. The core of cholesterol esters is enclosed in a layer of phospholipid and unesterified cholesterol molecules. The phospholipids are arrayed so that their hydrophilic heads are on the outside, thus allowing LDL-cholesterol to circulate through the blood.

However, too much cholesterol or LDL-cholesterol in the bloodstream is typically a major risk factor for cardiovascular disease. For example, excessive cholesterol can lead to formation of atheroscleromatous plaques. These plaques can cause narrowing and hardening of the arteries (i.e., atherosclerosis), which can impede blood flow and lead to a heart attack or stroke. In addition, relatively small atheroscleromatous plaques can become destabilized due to, for example, degradation of the connective tissue (i.e., collagen) "cap." Destabilization of the plaques can result in rupture of the plaque and thrombosis, which can lead to myocardial infarction.

Another lipoprotein that can combine with cholesterol is high density lipoprotein (HDL). HDL typically transports cholesterol to the liver. The liver metabolizes cholesterol, thus removing it from the body. Therefore, HDL is beneficial since it aids the removal of excess cholesterol from the circulation.

Another risk factor that has been associated with cardiovascular disease is C-reactive protein (CRP), which can be measured in serum or plasma. CRP is released by the body in response to acute injury, infection or other inflammation-inducing conditions, such as atherosclerosis. The release of CRP in response to inflammation has been proposed as a potential biomarker for cardiovascular diseases, due to, for example, atherosclerosis. Accordingly, current research is focusing on developing drugs that inhibit CRP, and thus decrease the incidence of such diseases (Taubes, 2002. *Science* 296:242–245). For example, recent studies have shown that treatment with pravastatin (statin) appears to result in reduced levels of CRP (Ridker et al. 1999. *Circulation* 100:230–235).

Accordingly, elevated levels of LDL-cholesterol or CRP are serious predictors of cardiovascular disease. Elevated levels of both LDL-cholesterol and CRP are synergetic predictors of cardiovascular disease. Therefore, patients with both elevated levels of LDL-cholesterol and CRP have an increased risk for developing cardiovascular disease.

Current treatments for lowering cholesterol, LDL-cholesterol, or CRP include a class of drugs known as statins. Statins generally alter the metabolism of various constituents within the cholesterol metabolic pathway. These drugs typically reduce serum/plasma LDL-cholesterol levels and CRP levels.

However, statins are associated with numerous side effects, including elevation of plasma triglycerides, increased liver aminotransferase activity, abdominal discomfort, nausea, vomiting, diarrhea, malaise, QT interval prolongation, and decreased high-density lipoprotein levels. These side effects limit the effectiveness of statins.

The compound tetracycline is a member of a class of antibiotic compounds that is referred to as the tetracyclines, tetracycline compounds, tetracycline derivatives and the like. The compound tetracycline exhibits the following general structure:

Structure A

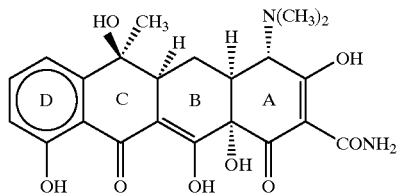

The numbering system of the tetracycline ring nucleus is as follows:

Structure B

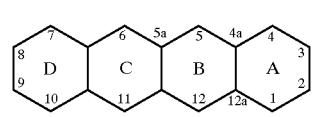

Tetracycline, as well as the terramycin and aureomycin derivatives, exist in nature, and are well known antibiotics. Natural tetracyclines may be modified without losing their antibiotic properties, although certain elements must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5–9 of the tetracycline ring system may be modified without the complete loss of antibiotic properties.

In addition to their antibacterial properties, tetracyclines have been described as having a number of other uses. For example, tetracyclines are also known to inhibit the activity of collagen destructive enzymes, produced by mammalian (including human) cells and tissues, by non-antibiotic mechanisms. Such enzymes include the matrix metalloproteinases (MMPs), including collagenases (MMP-1, MMP-8 and MMP-13), gelatinases (MMP-2 and MMP-9), and others (e.g. MMP-12, MMP-14). See Golub et al., *J Periodont. Res.* 20:12–23 (1985); Golub et al. *Crit. Revs. Oral Biol. Med.* 2:297–322 (1991); U.S. Pat. Nos. 4,666,897; 4,704,383; 4,935,411; 4,9354,412. Also, tetracyclines have been known to inhibit wasting and protein degradation in mammalian skeletal muscle, U.S. Pat. No. 5,045,538; to inhibit inducible NO synthase, U.S. Pat. Nos. 6,043,231 and 5,523, 297; to inhibit phospholipase $A_2$, U.S. Pat. Nos. 5,789,395 and 5,919,775; and to enhance IL-10 production in mammalian cells. Tetracyclines have also been found to be useful for reducing CRP levels, U.S. application Ser. No. 60/395, 466. These properties cause the tetracyclines to be useful in treating a number of diseases.

Several prior art references disclose the effect of tetracyclines on serum cholesterol levels. Some of these references report that tetracyclines had no effect on serum cholesterol. For example, Korpela et al. (*Scand. J. Gastroenterol.* 1984, 19:401–404) reported that administration of oxytetracycline had no effect on serum cholesterol and LDL-cholesterol in humans. Similarly, Samuel et al (*Circ. Res.* 1973. 33:393–402) disclosed that tetracycline had no effect on serum cholesterol levels in humans. Also, Berchev et al. showed that chlortetracycline either has no effect or increases serum cholesterol levels in cholesterol-fed rabbits.

In contrast, Bocker et al. (*Arzneimittelforschung* 1981. 31:211.8–2120), Shaddad et al. (*Comp. Biochem. Physiol.* 1985. 80:375–380), and Pigatto et al. *Dermatologica*. 1986. 172:154–159) reported that tetracyclines (e.g., tetracycline, doxycycline, oxytetracycline, and minocycline) reduce serum cholesterol levels. Similarly, Samuel et al. (*Circ. Res.* 1973. 33:393–402) reported that chlortetracycline reduces serum cholesterol levels and also reduces levels in patients with hypercholesterolemia.

Therefore, the prior art references are not consistent regarding the effect of tetracyclines on serum cholesterol levels. Furthermore, these references disclose studies on the effect of cholesterol levels by administering antibacterial tetracyclines. However, a disadvantage of using antibacterial tetracyclines is the development of antibiotic resistance to the tetracyclines and to other antibiotics (e.g., pan-antibiotic resistance). The possibility of using non-antibacterial tetracyclines was not disclosed in the prior art.

Thus, it is one object of the present invention to provide a method for decreasing elevated serum/plasma LDL-cholesterol levels. It would be especially desirable to provide a method for decreasing elevated serum/plasma LDL-cholesterol levels and C-reactive protein levels. Decreasing LDL-cholesterol levels and C-reactive protein levels would be surprising since it has been reported in the prior art that there is a lack of correlation between cholesterol levels and CRP levels in patients with cardiovascular diseases (Ridker, P et al. *New England Journal of Medicine* 2002. 347:1557–1565; Albert et al. *JAMA* 2001. 286:64–70; and Golub et al. unpublished data, see Example 2).

SUMMARY OF THE INVENTION

It has now been discovered that these and other objectives can be achieved by the present invention. The present invention relates to a method for decreasing elevated serum/plasma low density lipoprotein-cholesterol levels in a mammal in need thereof. The method comprises administering to the mammal an effective amount of a tetracycline formulation.

The present invention further relates to a method for decreasing elevated serum/plasma low density lipoprotein-cholesterol levels and C-reactive protein levels in a mammal in need thereof. The method comprises administering to the mammal an effective amount of a tetracycline formulation.

DETAILED DESCRIPTION OF THE INVENTION

The invention is based on the surprising discovery by the inventors that administration of a tetracycline formulation decreases elevated serum/plasma low density lipoprotein (LDL)-cholesterol levels. It is especially surprising that the tetracycline formulation can also be used for decreasing elevated serum/plasma LDL-cholesterol levels and C-reactive protein (CRP) levels.

Elevated and normal levels of LDL-cholesterol are known to those skilled in the art. For example, LDL-cholesterol levels greater than about 100 mg % (i.e., 100 mg LDL-cholesterol per 100 ml of blood) are typically considered elevated in humans.

Elevated and normal levels of CRP are also known to those skilled in the art. For example, CRP levels greater than about 0.11 milligrams per deciliter of blood (mg/dL) are generally considered elevated in humans. A decrease in the level of elevated CRP can occur before, during, or after a decrease in the level of elevated LDL-cholesterol.

An elevated level of serum/plasma LDL-cholesterol or serum/plasma CRP is considered to be decreased if the level of LDL-cholesterol or CRP is measurably lower after treatment than the level before treatment. Preferably, the methods of the present invention decrease the levels of LDL-cholesterol and/or CRP levels to normal levels. In humans, a normal level of LDL-cholesterol is generally less than about 100 mg %. A level of CRP less than about 0.11 mg/dL is typically considered normal in humans.

The method of the invention comprises administering an effective amount of a tetracycline formulation. In this specification, a tetracycline formulation comprises an antibacterial tetracycline compound, a non-antibacterial tetracycline compound, or a pharmaceutically acceptable salt thereof in a pharmaceutical carrier.

The effective amount of a tetracycline formulation administered is any amount effective for decreasing elevated serum/plasma LDL-cholesterol levels or decreasing elevated serum/plasma LDL-cholesterol levels and CRP levels in a mammal in need thereof. The actual preferred amounts of the tetracycline formulation in a specified case will vary according to various factors that are well known in the art, such as the particular composition formulated, the mode of application, and the particular subject being treated. The appropriate amount of the tetracycline formulation can readily be determined by those skilled in the art.

The minimal amount of a tetracycline formulation administered to a mammal is the lowest amount capable of decreasing elevated levels of LDL-cholesterol or of LDL-cholesterol and CRP. The maximal amount for a mammal is the highest effective amount that does not cause undesirable or intolerable side effects.

Antibacterial tetracycline compounds are administered in an amount that: (i) is effective in decreasing elevated serum/plasma LDL-cholesterol levels or an amount that is effective in decreasing elevated serum/plasma LDL-cholesterol levels and CRP levels, but (ii) has substantially no antibacterial activity. An amount has substantially no antibacterial activity if the amount does not significantly prevent the growth of bacteria. Preferably, the amount also does not result in the emergence of antibiotic-resistant bacteria. Such amounts are referred to herein as a "sub-antibacterial amount."

For example, sub-antibacterial amounts of antibacterial tetracycline compounds may be administered in a minimum amount which is approximately about 10%, preferably about 25%, and more preferably about 40% of the antibacterial amount. The maximum sub-antibacterial amount of an antibacterial tetracycline compound is approximately about 80%, preferably about 70%, and more preferably about 60% of the antibacterial amount.

Some examples of antibacterial amounts of members of the tetracycline family include 100 mg/day of doxycycline, 100 mg/day of minocycline, 250 mg of tetracycline four times a day, 1000 mg/day of oxytetracycline, 600 mg/day of demeclocycline and 600 mg/day of lymecycline.

Some examples of antibacterial tetracycline compounds include doxycycline, minocycline, tetracycline, oxytetracycline, chlortetracycline, demeclocycline, lymecycline and their pharmaceutically acceptable salts. Doxycycline is preferably administered as its hyclate salt or as a hydrate, preferably monohydrate.

As stated above, the tetracycline formulation also can comprise a non-antibacterial tetracycline compound. Non-antibacterial tetracycline compounds are structurally related to the antibacterial tetracyclines, but have had their antibiotic activity substantially or completely eliminated by chemical modification. For example, changes to the basic ring system or replacement of the substituents at positions 4 and 10–12a generally lead to synthetic tetracyclines with substantially less or effectively no antibacterial activity. Non-antibiotic chemically modified tetracyclines are referred to herein as CMTs.

For example, non-antibacterial tetracycline compounds are capable of achieving antibacterial activity comparable to that of tetracycline compounds at concentrations at least about ten times, preferably at least about twenty five times, greater than that of doxycycline.

invention are disclosed in international PCT application WO 01/87823. All such generic and specific compounds disclosed in PCT application WO 01/87823 are hereby incorporated by reference.

Derivatives of CMTs can also be used. Derivatives of CMTs include any compound derived from a CMT disclosed above by adding a substituent to the 7, 8, or 9 position of the tetracycline ring nucleus. Some examples of substituents include halo (e.g., F, Cl, Br, and I); nitro; hydroxy; alkyl carbonyl; alkyl carbonyloxy; alkyl amido; amino; alkyl amino; dialkyl amino; phenyl, carboxylate, etc., wherein alkyl represents $C_1$–$C_{16}$, preferably $C_1$–$C_4$, straight chain or branched alkyl (e.g., methyl, ethyl, isopropyl).

For example, some derivatives of CMT-3 include:

| | |
|---|---|
| CMT-301 | 7-bromo-6-demethyl-6-deoxy-4-dedimethylaminotetracycline |
| CMT-302 | 7-nitro-6-demethyl-6-deoxy-4-dedimethylaminotetracycline |
| CMT-303 | 9-nitro-6-demethyl-6-deoxy-4-dedimethylaminotetracycline |
| CMT-304 | 7-acetamido-6-demethyl-6-deoxy-4-dedimethylaminotetracycline |
| CMT-305 | 9-acetamido-6-demethyl-6-deoxy-4-dedimethylaminotetracycline |
| CMT-306 | 9-dimethylamino-6-demethyl-6-deoxy-4-dedimethylaminotetracycline |
| CMT-307 | 7-amino-6-demethyl-6-deoxy-4-dedimethylaminotetracycline |
| CMT-308 | 9-amino-6-demethyl-6-deoxy-4-dedimethylaminotetracycline |
| CMT-309 | 9-dimethylaminoacetamido-6-demethyl-6-deoxy-4-dedimethylaminotetracycline |
| CMT-310 | 7-dimethylamino-6-demethyl-6-deoxy-4-dedimethylaminotetracycline |
| CMT-311 | 9-palmitamide-6-demethyl-6-deoxy-4-dedimethylaminotetracycline |
| CMT-312 | 2-CONHCH$_2$-pyrrolidin-1-yl-6-demethyl-6-deoxy-4-dedimethylaminotetracycline |
| CMT-313 | 2-CONHCH$_2$-piperidin-1-yl-6-demethyl-6-deoxy-4-dedimethylaminotetracycline |
| CMT-314 | 2-CONHCH$_2$-morpholin-1-yl-6-demethyl-6-deoxy-4-dedimethylaminotetracycline |
| CMT-315 | 2-CONHCH$_2$-piperazin-1-yl-6-demethyl-6-deoxy-4-dedimethylaminotetracycline |

Examples of chemically modified non-antibacterial tetracyclines (CMTs) include those that lack the dimethylamino group at position 4 of the tetracycline ring structure, e.g.,:

4-dedimethylaminotetracycline (CMT-1), 6-demethyl-6-deoxy-4-de(dimethylamino)tetracycline (CMT-3), 7-chloro-4-de(dimethylamino)tetracycline (CMT-4), 4-hydroxy-4-de(dimethylamino)tetracycline (CMT-6), 4-de(dimethylamino)-12α-deoxytetracycline (CMT-7), 6-deoxy-5α-hydroxy-4-de(dimethylamino)tetracycline (CMT-8), 4-dedimethylamino-12α-deoxyanhydrotetracycline (CMT-9), 7-dimethylamino-6-demethyl-6-deoxy-4-de(dimethylamino)tetracycline (CMT-10), 4-dedimethylamino-5-oxytetracycline, 5α,6-anhydro-4-hydroxy-4-de(dimethylamino)tetracycline, 4-de(dimethylamino)-11-hydroxy-12α-deoxytetracycline, 12α-deoxy-4-deoxy-4-de(dimethylamino)tetracycline, and 12α,4α-anhydro-4-de(dimethylamino)tetracycline.

Further examples of tetracyclines modified for reduced antibacterial activity include 6-α-benzylthiomethylenetetracycline, the mono-N-alkylated amide of tetracycline, 6-fluoro-6-demethyltetracycline, 11α-chlorotetracycline, tetracyclinonitrile (CMT-2), and tetracycline pyrazole (CMT-5).

Further examples of generic and specific tetracycline compounds that are suitable for use in the methods of the Some derivatives of CMT-8 include:

| | |
|---|---|
| CMT-801 | 9-acetamido-4-dedimethylaminodoxycycline |
| CMT-802 | 9-dimethylaminoacetamido-4-dedimethylaminodoxycycline |
| CMT-803 | 9-palmitamide-4-dedimethylaminodoxycycline |
| CMT-804 | 9-nitro-4-dedimethylaminodoxycycline |
| CMT-805 | 9-amino-4-dedimethylaminodoxycycline |
| CMT-806 | 9-dimethylamino-4-dedimethylaminodoxycycline |
| CMT-807 | 2-CONHCH$_2$-pyrrolidin-1-yl-4-dedimethylaminodoxycycline |
| CMT-808 | 2-CONHCH$_2$-piperidin-1-yl-4-dedimethylaminodoxycycline |
| CMT-809 | 2-CONHCH$_2$-piperazin-1-yl-4-dedimethylaminodoxycycline |

Some derivatives of CMT-10 include:

| | |
|---|---|
| CMT-1001 | 7-trimethylammonium-4-dedimethylaminosancycline |
| CMT-1002 | 9-nitro-4-dedimethylaminominocycline |

An effective amount of a CMT can be any amount that decreases elevated levels of LDL-cholesterol or of LDL-cholesterol and CRP. The effective amount can be determined during pre-clinical trials and clinical trials by methods familiar to physicians and clinicians. For example, an effective amount of a CMT can be from about 1.0 mg/day to about 2000 mg/day.

The invention also includes pharmaceutically acceptable salts of the above disclosed compounds. "Pharmaceutically acceptable salts" mean salts that do not substantially contribute to the toxicity of the compound. Such salts are formed by well known procedures.

Some examples of suitable salts include acid addition salts of basic tetracycline compounds. Suitable acids include mineral acids and organic acids. Some examples of mineral acids include hydrochloric, hydriodic, hydrobromic, phosphoric, metaphosphoric, nitric and sulfuric acids. Some examples of organic acids include tartaric, acetic, citric, malic, benzoic, glycollic, gluconic, gulonic, succinic, arylsulfonic, e.g. p-toluenesulfonic acids, and the like.

The tetracycline formulations are administered to a mammal in need thereof. Mammals in need of decreasing serum/plasma LDL-cholesterol levels or decreasing serum/plasma LDL-cholesterol levels and CRP levels is any mammal which has an elevated serum/plasma LDL-cholesterol level or elevated serum/plasma LDL-cholesterol and CRP levels. For example, mammals suffering from a cardiovascular disease often have elevated serum/plasma LDL-cholesterol levels or elevated serum/plasma LDL-cholesterol levels and CRP levels.

The cardiovascular disease can be any disease of the heart, as well as disorders of the blood vessels. Examples of such diseases or disorders include, but are not limited to, atherosclerosis, myocardial infarction, hypercholesterolemia, stroke due to, for instance, rupture of a plaque in e.g., the carotid artery, and cerebral vascular disease.

Other diseases and conditions that are associated with elevated levels of serum/plasma LDL-cholesterol levels or elevated serum/plasma LDL-cholesterol and CRP levels include, for example, diabetes and estrogen deficiency, as occurs, for example, in post-menopausal women, women with hysterectomies, and women with one or more ovaries removed.

Any mammal can be treated in accordance with the present invention. Mammals include, for example, humans, baboons, and other primates, as well as pet animals such as dogs and cats, laboratory animals such as rats and mice, and farm animal such as horses, sheep, and cows.

Synthesis of CMTs

The chemically modified tetracycline compounds can be synthesized by any of the methods known in the art. Suitable methods for synthesizing CMTs include, for example, those described in Mitscher, L. A., *The Chemistry of the Tetracycline Antibiotics*, Marcel Dekker, New York (1978), Ch. 6, and U.S. Pat. Nos. 4,704,383 and 5,532,227.

After synthesis, the compounds can be conveniently purified by standard methods known in the art. Some suitable examples include crystallization from a suitable solvent or partition-column chromatography.

Modes of Administration

The tetracycline formulation may be administered alone or as an adjunct with other conventional drugs for lowering cholesterol or CRP.

The tetracycline formulations may be administered by any method known in the art. Some examples of suitable modes of administration include oral and systemic administration. Systemic administration can be enteral or parenteral. Enteral administration is a preferred route of delivery of the tetracycline formulations. Liquid or solid (e.g., tablets, gelatin capsules) formulations can be employed.

Parenteral administration of the tetracycline formulations include, for example intravenous, intramuscular, and subcutaneous injections. For instance, a tetracycline formulation may be administered to a mammal by sustained release, as is known in the art. Sustained release administration is a method of drug delivery to achieve a certain level of the drug over a particular period of time.

Other routes of administration include oral, topical, intrabronchial, or intranasal administration. For oral administration, liquid or solid formulations may be used. Some examples of fomulations suitable for oral administration include tablets, gelatin capsules, pills, troches, elixirs, suspensions, syrups, and wafers. Intrabronchial administration can include an inhaler spray. For intranasal administration, administration of a tetracycline formulation can be accomplished by a nebulizer or liquid mist.

The tetracycline formulation comprises a tetracycline compound in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The tetracycline formulations may also comprises one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the tetracycline compound.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example sodium chloride, or sodium/potassium phosphate, respectively. Preferably, the buffering agent maintains the pH of the tetracycline formulation in the range of about 5.5 to about 7.5. The salt and/or buffering agent is also useful to maintain the osmolality at a level suitable for administration to a mammal. Preferably the salt or buffering agent is present at a roughly isotonic concentration of about 150 mM to about 300 mM.

The tetracycline formulations may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as for example a morphine derivative; or an isotonic agent etc., such as described above. As a further precaution against oxidation or other spoilage, the tetracycline formulations may be stored under nitrogen gas in vials sealed with impermeable stoppers.

EXAMPLES

Example 1

Administration of Doxycycline at a Sub-Antibacterial Dose Decreases Plasma LDL-cholesterol Acute coronary syndrome patients prescribed statins and still exhibited elevated cholesterol levels (total of 3 patients) were administered doxycycline at a sub-antibacterial dose (20 mg twice a day) for six months. After six months, the cholesterol fractions were then measured (Table 1). Table 1: The Effect of a 6-Month Regimen of Sub-Antibacterial Doxycycline on Cholesterol Values in Plasma of Acute Coromary Syndrome Patients with Elevated Baseline Cholesterol

| | Cholesterol Fractions (mg %) | | | |
|---|---|---|---|---|
| | Total Cholesterol | LDL-Cholesterol | HDL-Cholesterol | HDL/Cholesterol |
| Baseline Level | 231 ± 20 | 155 ± 9 | 48 ± 17 | 0.21 |
| 6 Month Level | 190 ± 20 | 107 ± 12 | 48 ± 18 | 0.25 |
| Change Due to Treatment | 18% Reduction | 31% Reduction | No Change | 19% Increase |

After six-months of sub-antibacterial doxycycline treatment, total cholesterol was reduced by about 18%. The sub-antibacterial doxycycline reduced total plasma cholesterol to normal levels. A 19% increase in the ratio of HDL-cholesterol to total cholesterol was also observed.

The most dramatic reduction observed was the statistically significant 31% decrease in LDL-cholesterol ($p=0.033$) after 6-months of sub-antibacterial doxycycline treatment. Sub-antibacterial doxycycline reduced the level of LDL-cholesterol to around normal levels.

Example 2
Lack of Correlation Between CRP Levels and LDL-Cholesterol Levels

Plasma of 30 patients who presented with acute coronary syndrome were analyzed, at baseline, for levels of high sensitivity CRP and total cholesterol, LDL-cholesterol, and HDL-cholesterol. No correlation was found between high sensitivity CRP and each of the following: total cholesterol, LDL-cholesterol, and HDL-cholesterol.

Example 3
Administration of Doxycycline at a Sub-Antibacterial Dose Decreases LDL-cholesterol and CRP Levels in Diabetic Patients Diabetic patients with elevated levels of cholesterol and CRP levels were administered 20 mg of doxycycline twice a day for at least two months. Doxycycline decreased LDL-cholesterol and improved the patients lipid profile. A decrease in CRP levels was also observed.

What is claimed is:

1. A method for decreasing elevated serum/plasma low density lipoprotein-cholesterol levels in a mammal in need thereof, the method comprising administering to the mammal an effective amount of a tetracycline formulation.

2. A method according to claim 1, wherein the tetracycline formulation comprises a non-antibacterial tetracycline.

3. A method according to claim 1, wherein the tetracycline formulation comprises a antibacterial tetracycline at a sub-antibacterial amount.

4. A method according to claim 3, wherein the antibacterial tetracycline is doxycycline.

5. A method according to claim 3, wherein the antibacterial tetracycline is minocycline.

6. A method according to claim 2, wherein the non-antibacterial tetracycline is CMT-3.

7. A method according to claim 2, wherein the non-antibacterial tetracycline is CMT-308.

8. A method according to claim 2, wherein the non-antibacterial tetracycline is CMT-8.

9. A method according to claim 2, wherein the non-antibacterial tetracycline is CMT-10.

10. A method according to claim 2, wherein the non-antibacterial tetracycline is CMT-1002.

11. A method for decreasing elevated serum/plasma low density lipoprotein-cholesterol levels and C-reactive protein levels in a mammal in need thereof, the method comprising administering to the mammal an effective amount of a tetracycline formulation.

12. A method according to claim 11, wherein the tetracycline formulation comprises a non-antibacterial tetracycline.

13. A method according to claim 11, wherein the tetracycline formulation comprises a antibacterial tetracycline at a sub-antibacterial amount.

14. A method according to claim 13, wherein the antibacterial tetracycline is doxycycline.

15. A method according to claim 13, wherein the antibacterial tetracycline is minocycline.

16. A method according to claim 12, wherein the non-antibacterial tetracycline is CMT-3.

17. A method according to claim 12, wherein the non-antibacterial tetracycline is CMT-308.

18. A method according to claim 12, wherein the non-antibacterial tetracycline is CMT-8.

19. A method according to claim 12, wherein the non-antibacterial tetracycline is CMT-10.

20. A method according to claim 12, wherein the non-antibacterial tetracycline is CMT-1002.

* * * * *